United States Patent
Tagawa (10) Patent No.: US 9,476,844 B2
(45) Date of Patent: Oct. 25, 2016

(54) RADIOGRAPHIC APPARATUS AND AN IMAGE PROCESSING METHOD THEREFORE

(71) Applicant: SHIMADZU CORPORATION, Kyoto-shi, Kyoto (JP)

(72) Inventor: Yusuke Tagawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 237 days.

(21) Appl. No.: 14/154,922

(22) Filed: Jan. 14, 2014

(65) Prior Publication Data

US 2014/0205058 A1    Jul. 24, 2014

(30) Foreign Application Priority Data

Jan. 21, 2013    (JP) .................................. 2013-008437

(51) Int. Cl.
*G01N 23/04* (2006.01)
*G06T 11/00* (2006.01)

(52) U.S. Cl.
CPC .......... *G01N 23/046* (2013.01); *G06T 11/005* (2013.01); *G01N 2223/3304* (2013.01); *G01N 2223/419* (2013.01); *G01N 2223/6113* (2013.01)

(58) Field of Classification Search
CPC ..................... G01N 23/046; G01N 2223/419; G01N 2223/3304; G01N 2223/6113; A61B 6/027; A61B 6/032; A61B 6/583; A61B 6/587; G06T 11/005; G06T 11/006
See application file for complete search history.

(56) References Cited

U.S. PATENT DOCUMENTS

2004/0252811 A1* 12/2004 Morita ................. A61B 6/466
378/207
2008/0212734 A1* 9/2008 Kasperl ................ G01T 1/2985
378/4

(Continued)

FOREIGN PATENT DOCUMENTS

CN          102652674 A       9/2012
JP          2003329616 A1  *  11/2003    .............. G01N 23/04

(Continued)

OTHER PUBLICATIONS

Machine translation of JP2003329616A1 published in Nov. 2003.*

(Continued)

*Primary Examiner* — Glen Kao
(74) *Attorney, Agent, or Firm* — McDermott Will & Emery LLP (57) ABSTRACT

Initial values $\hat{A}_1 \hat{P}_1 \hat{M}_1 \ldots \hat{A}_n \hat{P}_n \hat{M}_n$ of parameters representing a geometric relationship between an X-ray tube, a stage and a flat panel X-ray detector are estimated, a least squares solution $(\hat{p}_W)_i$ of characteristic point three-dimensional coordinates is estimated, and only limited parameters are updated until reprojection square errors converge. Thus, based on known radiographic conditions, initial values of the parameters are estimated, and a nonlinear optimization operation is carried out on only the parameters considered, in view of mechanisms and drive characteristics of the apparatus, to have large errors between the initial values of the parameters and the parameters at a time when radiography is actually carried out. As a result, the calculation can be speeded up, while securing the convergence accuracy of the nonlinear optimization operation, by using the radiographic conditions, i.e. information on tomography.

6 Claims, 8 Drawing Sheets

(56) References Cited

U.S. PATENT DOCUMENTS

| | | |
|---|---|---|
| 2009/0175497 A1 | 7/2009 | Anai et al. |
| 2009/0175498 A1 | 7/2009 | Kochi et al. |

FOREIGN PATENT DOCUMENTS

| | | |
|---|---|---|
| JP | 3694833 B2 | 9/2005 |
| JP | 2007-048068 A | 2/2007 |
| JP | 2009-014629 A | 1/2009 |
| JP | 2010-002221 A | 1/2010 |
| JP | 4415762 B2 | 2/2010 |

OTHER PUBLICATIONS

First Office Action Chinese Patent Application No. 201410028530.7 dated Dec. 1, 2015 with English translation.

* cited by examiner

RADIOGRAPHIC APPARATUS AND AN IMAGE PROCESSING METHOD THEREFORE

TECHNICAL FIELD

This invention relates to a radiographic apparatus and an image processing method therefor, for performing radiography based on projection images obtained by detecting, with a radiation detecting device, radiation emitted from a radiation emitting device and transmitted through an object.

BACKGROUND ART

Description will be made taking X-rays as an example of radiation. The object may be a mounted substrate, a through hole/pattern/solder joint of a multilayer substrate, an electronic component before mounting such as an integrated circuit (IC) arranged on a palette, a casting such as of metal, or a molded article such as a videocassette recorder. Specifically, it is used for inspection of electronic components (eg inspection of wiring on substrates, and inspection of BGA (Ball Grid Array), solder joints, voids) and for inspection of internal defects of these objects.

Figure 1:
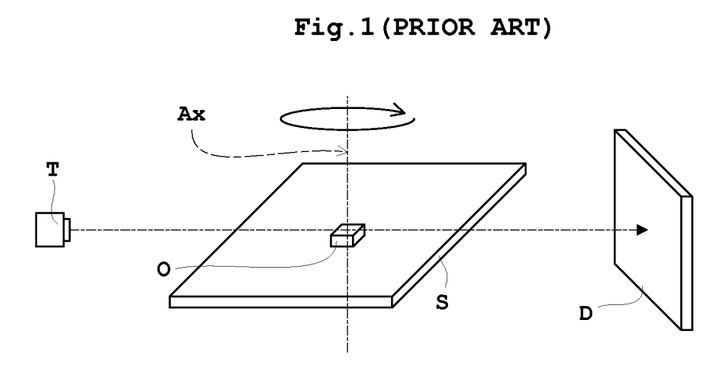
FIG. 1 is a schematic view of conventional radiography.

With a CT (Computed Tomography) apparatus known conventionally, as shown in FIG. 1, an object O is placed on a rotary stage S between an X-ray tube T (radiation emitting device) and an X-ray detector D (radiation detecting device) arranged opposite each other. The object O placed on the rotary stage S is rotated by rotating the rotary stage S about an axis of rotation Ax extending perpendicular to the surface of the rotary stage S. By rotating the object O about the axis of rotation Ax in this way, projection images of the object O are obtained from various angles, and a three-dimensional image is calculated by reconstructing these projection images.

When conducting X-ray inspection by tomography of an object having a very fine structure such as Ball Grid Array (BGA) or wiring, it is necessary to carry out radiography with an increased enlargement ratio. In order to increase the enlargement ratio, however, it is necessary to carry out radiography with the radiation source represented by the X-ray tube and the object brought close to each other. In the case of the object having a large planar shape, there arises a possibility that the X-ray tube and the object interfere each other. As a result, in order to avoid interference, the enlargement ratio cannot be increased too much.

Figure 2:
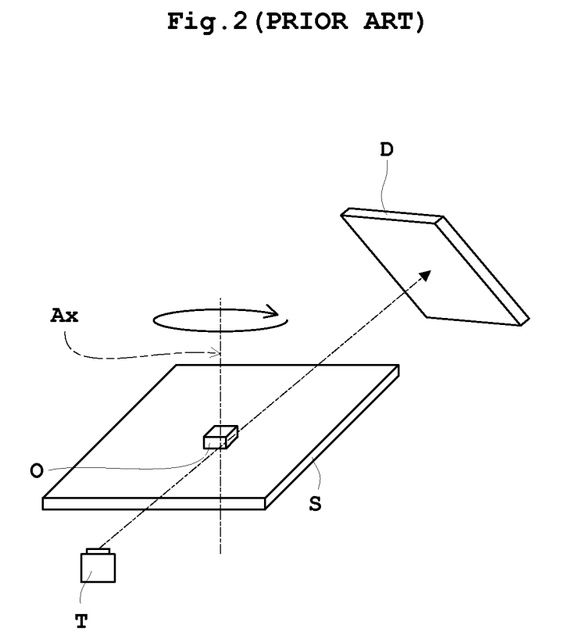
FIG. 2 is a schematic view of conventional oblique radiography.
Figure 3:
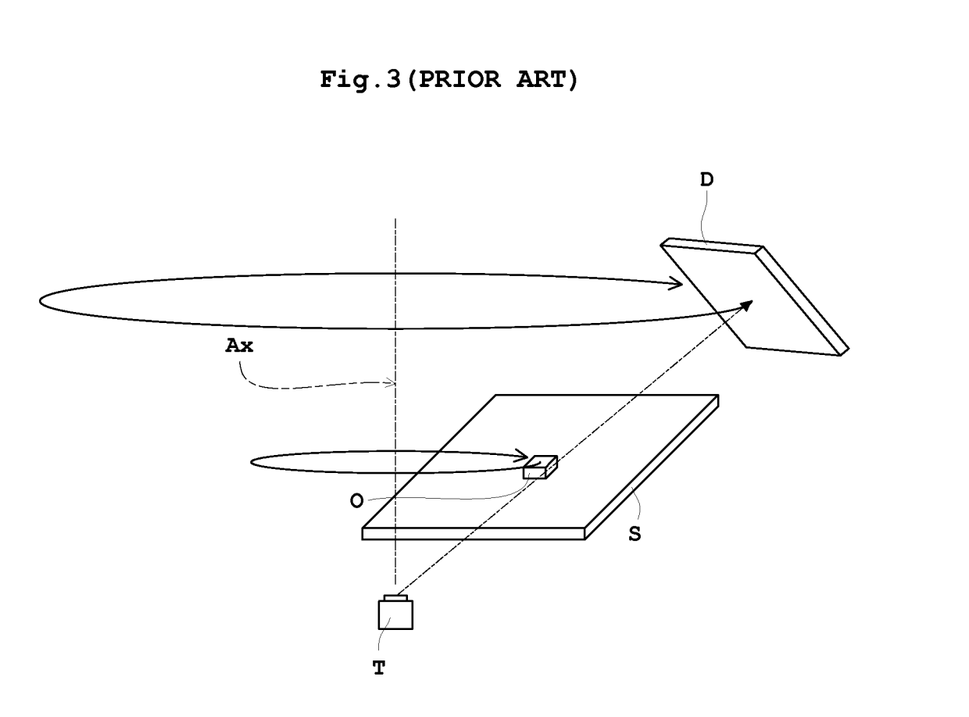
FIG. 3 is a schematic view of conventional oblique radiography in which a stage is put to parallel translation and an X-ray detector is driven to revolve synchronously with the stage movement.

So, planar CT (PCT: Planar Computed Tomography) is known, which carries out tomography, as shown in FIG. 2, with the X-ray tube T and X-ray detector D arranged in an oblique direction inclined by lamino angle from the axis of rotation Ax to avoid interference with the object O. Also for an X-ray fluoroscopic apparatus having no rotating mechanism for a stage, there is a method of realizing PCT, in which, as shown in FIG. 3, a stage S with an object O placed thereon is put to parallel translation to describe a circular path on a plane (level plane in FIG. 3) perpendicular to an axis of rotation Ax, and driving an X-ray detector D to revolve about the same axis of rotation Ax synchronously with the movement of stage S. See Patent Document 1: Japanese Unexamined Patent Publication No. 2010-2221, and Patent Document 2: Japanese Patent No. 3694833, for example.

Since, in the radiographing method of FIG. 3, the stage and the X-ray detector have drive mechanisms independent of each other, mechanisms and control are required to realize highly precise positioning and synchronization in order to acquire ideal tomographic scan paths, which results in increased cost. So, even where a disagreement occurs between actual scan paths and ideal scan paths, there is a method of calculating actual scan paths with high precision by calibration (correction) with a phantom for correction, and maintaining them as correction parameters for reconstruction. See Patent Document 3: Japanese Patent No. 4415762, for example. The correction parameter calculation at this time is the same problem setting as the camera calibration known in the field of computer vision, and a method such as Bundle Adjustment is known as a calculation algorithm.

The Bundle Adjustment method is a technique of calculating, from characteristic points extracted from images, three-dimensional coordinates of the characteristic points and parameters of a geometric model at the time of radiography by nonlinear optimization operation. Since repetitive operations are carried out at this time, computation time may become long due to various conditions such as a method of setting initial values, the number of characteristic points, the number of frames and an estimated number of parameters. So, methods of reducing computation time have been proposed. See Patent Document 4: Japanese Unexamined Patent Publication No. 2007-48068, and Patent Document 5: Japanese Unexamined Patent Publication No. 2009-14629, for example.

Patent Document 4, ie Japanese Unexamined Patent Publication No. 2007-48068, tackles as follows the problem that speeding up of an operation using conventional Jacobian matrix being a sparse matrix including many zeros cannot be applied directly because of an increase of unknown parameters when there are two or more types (such as point pattern and square pattern) in the amount of characteristic extracted from images. That is, the unknown parameters are divided into three or more and are put into a matrix form enabling a speed-up of operation, which are calculated by stages to realize shortening of the computation time.

Patent Document 5, ie Japanese Unexamined Patent Publication No. 2009-14629, tackles as follows the problem that the convergence of nonlinear optimization operation becomes poor and exerts an adverse influence on parameter calculation accuracy and computation time when an error occurs in matching between the frames of characteristic points extracted from images or when inappropriate characteristic points are extracted. That is, it seeks to attain a high precision and high speed of the nonlinear optimization operation by applying a robust estimating method (LmedS method or RANSAC method) which removes outliers at the time of evaluation function calculation, thereby to inhibit the influence of outliers.

PRIOR ART DOCUMENTS

Patent Documents

[Patent Document 1]
Unexamined Patent Publication No. 2010-2221
[Patent Document 2]
U.S. Pat. No. 3,694,833
[Patent Document 3]
U.S. Pat. No. 4,415,762
[Patent Document 4]
Unexamined Patent Publication No. 2007-48068
[Patent Document 5]
Unexamined Patent Publication No. 2009-14629

SUMMARY OF INVENTION

Technical Problem

However, Patent Document 4, ie Japanese Unexamined Patent Publication No. 2007-48068, shows a speed-up technique in a specific condition that there are two or more types in the amount of characteristics, which is irrelevant when extracting only characteristic points from images to execute the Bundle Adjustment method. Patent Document 5, ie Japanese Unexamined Patent Publication No. 2009-14629, is premised on inappropriate characteristic point extraction or incorrect matching of characteristic points between the frames, but there is little such influence (adverse influence on parameter calculation accuracy and computation time) when carrying out calibration in a controlled environment using a phantom for correction. This can hardly be said relevant to speeding up. The conventional methods include no proposal concerning a speed-up method tackling a problem that computation time for nonlinear optimization operation becomes long with increase in the number of parameters.

This invention has been made having regard to the state of the art noted above, and its object is to provide a radiographic apparatus and an image processing method therefor, which can speed up calculation while securing the convergence accuracy of nonlinear optimization operation.

Solution to Problem

To fulfill the above object, this invention provides the following construction.

A radiographic apparatus according to this invention comprises a stage for holding an object; and a radiation emitting device and a radiation detecting device arranged opposite each other across the stage; radiography being performed based on projection images obtained by detecting, with the radiation detecting device, radiation emitted from the radiation emitting device and transmitted through the object; the apparatus further comprising a driving device for driving at least one of the radiation emitting device and the stage in a state where the object or a phantom for correction is placed on the stage; a parameter calculating device for calculating parameters representing a geometric relationship between the radiation emitting device, the stage and the radiation detecting device by nonlinear optimization operation based on a plurality of projection images of the phantom for correction; a slice image calculating device for calculating slice images of the object based on a plurality of projection images of the object and the parameters, and when carrying out the calculation, reconstructing the images using those of the parameters suited to radiographic conditions at a time of radiographing the object; and a number of parameters limiting device for reducing and limiting, when calculating the parameters, the number of parameters calculated by nonlinear optimization operation, based on radiographic conditions at a time of radiographing the phantom for correction.

[Functions and effects] According to the radiographic apparatus in this invention, the parameter calculating device, based on a plurality of projection images of a phantom for correction, calculates parameters representing a geometric relationship between the radiation emitting device, stage and radiation detecting device by nonlinear optimization operation. Based on a plurality of projection images of an object and the above parameters (correction parameters), the slice image calculating device calculates slice images of the object, and when carrying out this calculation, reconstructs the images using parameters suited to radiographic conditions at the time of radiographing the object. At the time of this parameter calculation, based on the radiographic conditions when the phantom for correction is radiographed, the number of parameters limiting device reduces and limits the number of parameters to be calculated by nonlinear optimization operation. Thus, based on the known radiographic conditions, initial values of the parameters representing the geometric relationship between the radiation emitting device, stage and radiation detecting device are estimated, and the nonlinear optimization operation is carried out on only the parameters considered, in view of mechanisms and drive characteristics of the apparatus, to have large errors between the initial values of the parameters and the parameters at the time when radiography is actually carried out. As a result, the calculation can be speeded up, while securing the convergence accuracy of the nonlinear optimization operation, by using the radiographic conditions, i.e. information on tomography.

In the radiographic apparatus in this invention described above, it is preferred that, when radiographic conditions have been changed, the number of parameters limiting device described above reduces and limits the number of parameters calculated by nonlinear optimization operation, based on the changed radiographic conditions. For example, a nonlinear optimization operation is carried out just once after shipment or after installation of the apparatus, and the number of parameters is reduced and limited based on the changed radiographic conditions when the radiographic conditions have been changed. Not only drive errors of the drive line, but there exist installation errors occurring at the time of shipment and installation of each constituent element of the radiographic apparatus, which become errors in the initial values of the parameters. So, parameters including the installation errors are calculated by carrying out a nonlinear optimization operation just once after shipment or after installation of the apparatus, and estimation is made of only the parameters of portions relevant to the drive errors of the drive line when the radiographic conditions have been changed.

The timing of reducing and limiting the number of parameters is not limited only to the time when the radiographic conditions are actually changed. Since, for example, it is possible that drive errors of the drive line occur at the time the apparatus is powered on, the number of parameters may be reduced and limited based on the radiographic conditions at the power-on time after each operation to switch on the apparatus. A setting for reducing and limiting the number of parameters may be carried out automatically by the central processing unit (CPU) or the like which determines that the radiographic conditions have been changed, or manually by the operator, or by combination of the automatic and manual operations.

In the radiographic apparatus in this invention described above, it is preferred that the number of parameters limiting device limits the parameters calculated by nonlinear optimization operation to three parameters representing a coordinates positional relationship between the radiation emitting device and the stage. In a triaxial drive, for example, it is possible to set a limitation to three parameters when an enlargement ratio is changed, and when changing the distance (SID: Source Image Distance) a perpendicular is drawn from the radiation emitting device to the radiation detecting device. Since radiography is fluoroscopy, enlarged images are necessarily projected to the radiation detecting device. Therefore, the influence of drive errors of the radiation emitting device and the stage on the projection images is greater than the influence of drive errors of the radiation detecting device on the projection images. So, while securing the convergence accuracy of nonlinear optimization operation, the operation can be speeded up, by performing calculations limited to the three parameters representing the coordinates positional relationship between the radiation emitting device and the stage, which have a great influence.

In particular, that the driving device rotates the stage with an axis perpendicular to the surface of the stage set as the axis of rotation can be applied to the case of planar CT (PCT: Planar Computed Tomography) which emits radiation from the radiation emitting device in an oblique direction inclined by lamino angle from the axis of rotation. In planar CT (PCT), radiography can be performed with a higher enlargement ratio than in ordinary CT. With the higher enlargement ratio, the greater influence is exerted on projection images by drive errors of the radiation emitting device and the stage. This reduces an adverse influence on the convergence accuracy of evaluation function due to limiting to the three parameters.

In an image processing method for a radiographic apparatus comprising a stage for holding an object; and a radiation emitting device and a radiation detecting device arranged opposite each other across the stage; the radiography being performed based on projection images obtained by detecting, with the radiation detecting device, radiation emitted from the radiation emitting device and transmitted through the object; the image processing method in this invention comprises a number of parameters limiting step executed when calculating parameters representing a geometric relationship between the radiation emitting device, the stage and the radiation detecting device by nonlinear optimization operation based on a plurality of projection images of a phantom for correction, for reducing and limiting, when calculating the parameters, the number of parameters calculated by nonlinear optimization operation, based on radiographic conditions at a time of radiographing the phantom for correction.

[Functions and effects] According to the image processing method in this invention, at the time of parameter calculation, the number of parameters to be calculated by nonlinear optimization operation is reduced and limited based on the radiographic conditions when the phantom for correction is radiographed. Thus, based on the known radiographic conditions, initial values of the parameters representing the geometric relationship between the radiation emitting device, stage and radiation detecting device are estimated, and the nonlinear optimization operation is carried out on only the parameters considered, in view of mechanisms and drive characteristics of the apparatus, to have large errors having occurred between the initial values of the parameters and the parameters at the time when radiography is actually carried out. As a result, the calculation can be speeded up, while securing the convergence accuracy of the nonlinear optimization operation, by using the radiographic conditions, i.e. information on tomography.

Specifically, a parameter calculating step is provided for calculating the above-mentioned parameters by nonlinear optimization operation. The parameter calculating step includes a characteristic point three-dimensional coordinates estimating step, a reprojection coordinates calculating step, a reprojection square error calculating step, a convergence determining step and a parameter updating step. In the parameter updating step, only parameters limited in the above number of parameters limiting step are updated. In the characteristic point three-dimensional coordinates estimating step, based on characteristic points extracted from projection images of the phantom for correction and initial values of the parameters, three-dimensional coordinates of the characteristic points are estimated. In the reprojection coordinates calculating step, reprojection coordinates are calculated based on the characteristic point three-dimensional coordinates estimated in the characteristic point three-dimensional coordinates estimating step. In the reprojection square error calculating step, reprojection square errors are calculated based on the reprojection coordinates calculated in the reprojection coordinates calculating step and the above characteristic points. In the convergence determining step, convergence determination is made of the reprojection square errors calculated in the reprojection square error calculating step. And in the parameter updating step, when values of the reprojection square errors have not converged, the parameters are updated to reduce the values of the reprojection square errors, and at the time of this updating, only the parameters limited in the above number of parameters limiting step are updated. Thus, at the time of parameter updating, the number of parameters to be calculated is limited beforehand based on radiographic conditions. This can reduce the number of parameters to be updated in the parameter updating step, and calculation can be speeded up while securing the convergence accuracy of the nonlinear optimization operation.

Advantageous Effects of Invention

According to the radiographic apparatus in this in this invention and the image processing method therefor, at the time of parameter calculation, based on the radiographic conditions when the phantom for correction is radiographed, the number of parameters limiting device reduces and limits the number of parameters to be calculated by nonlinear optimization operation. Thus, based on the known radiographic conditions, initial values of the parameters representing the geometric relationship between the radiation emitting device, stage and radiation detecting device are estimated, and the nonlinear optimization operation is carried out on only the parameters considered, in view of mechanisms and drive characteristics of the apparatus, to have large errors having occurred between the initial values of the parameters and the parameters at the time when radiography is actually carried out. As a result, the calculation can be speeded up, while securing the convergence accuracy of the nonlinear optimization operation, by using the radiographic conditions, i.e. information on tomography.

DESCRIPTION OF EMBODIMENTS

[Embodiment]

An embodiment of this invention will be described hereinafter with reference to the drawings.

Figure 4:
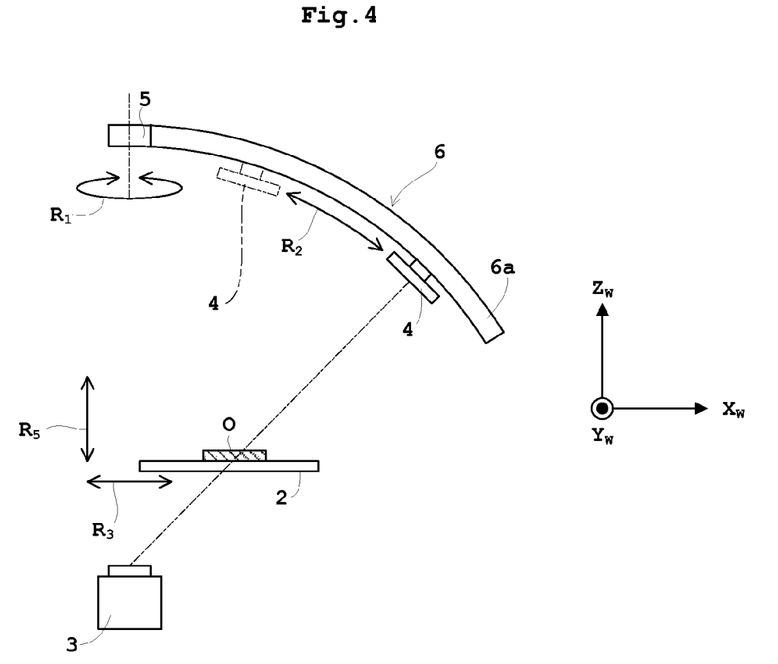
FIG. 4 is an outline schematic view of an X-ray inspection apparatus according to an embodiment.
Figure 5:
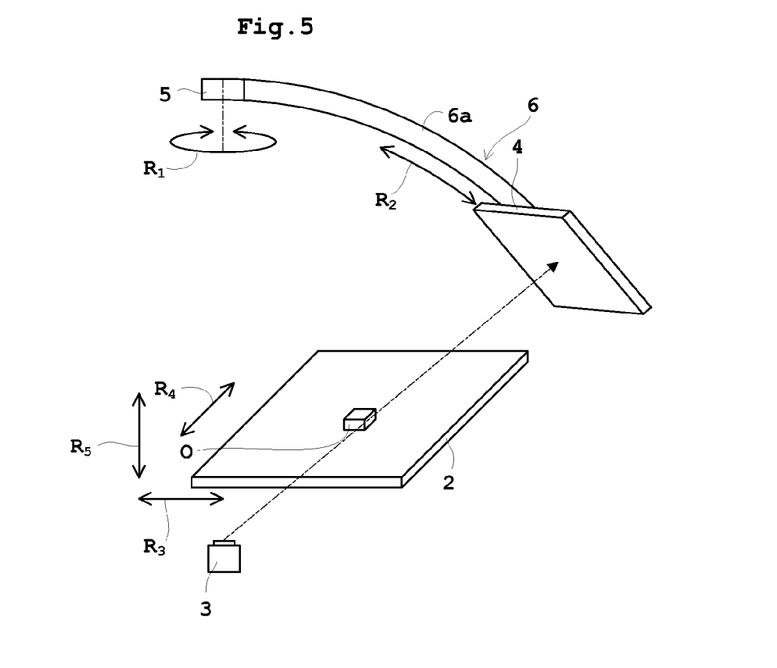
FIG. 5 is an outline perspective view of the X-ray inspection apparatus according to the embodiment.
Figure 6:
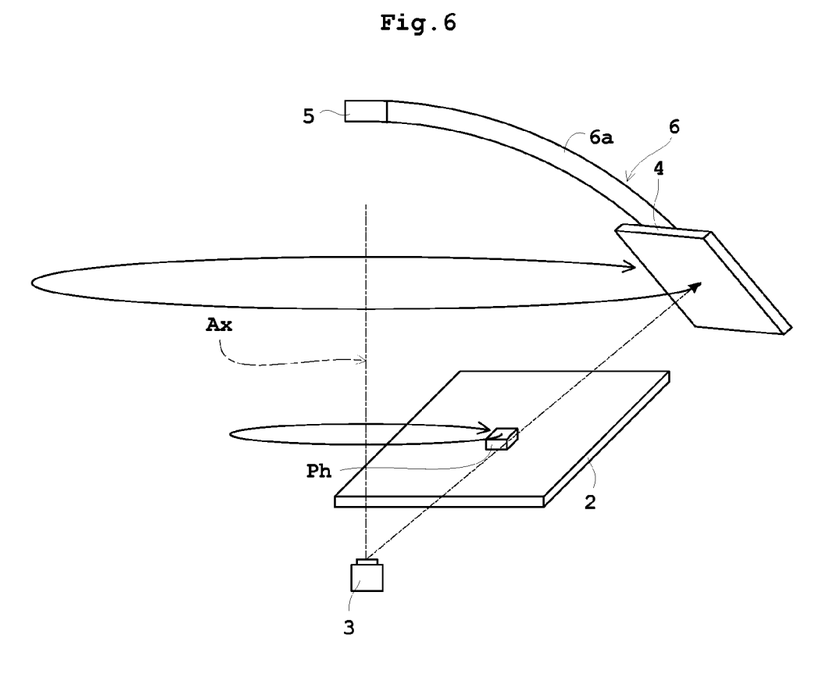
FIG. 6 is an outline perspective view of the X-ray inspection apparatus according to the embodiment illustrating a calibration method with a phantom for correction.
Figure 7:
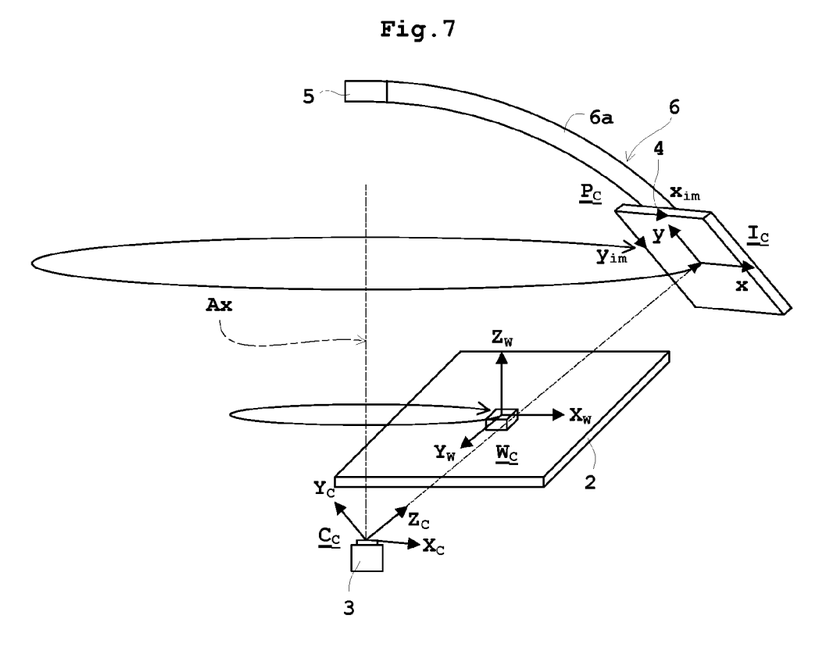
FIG. 7 is an outline perspective view of the X-ray inspection apparatus according to the embodiment illustrating each coordinate system.
Figure 8:
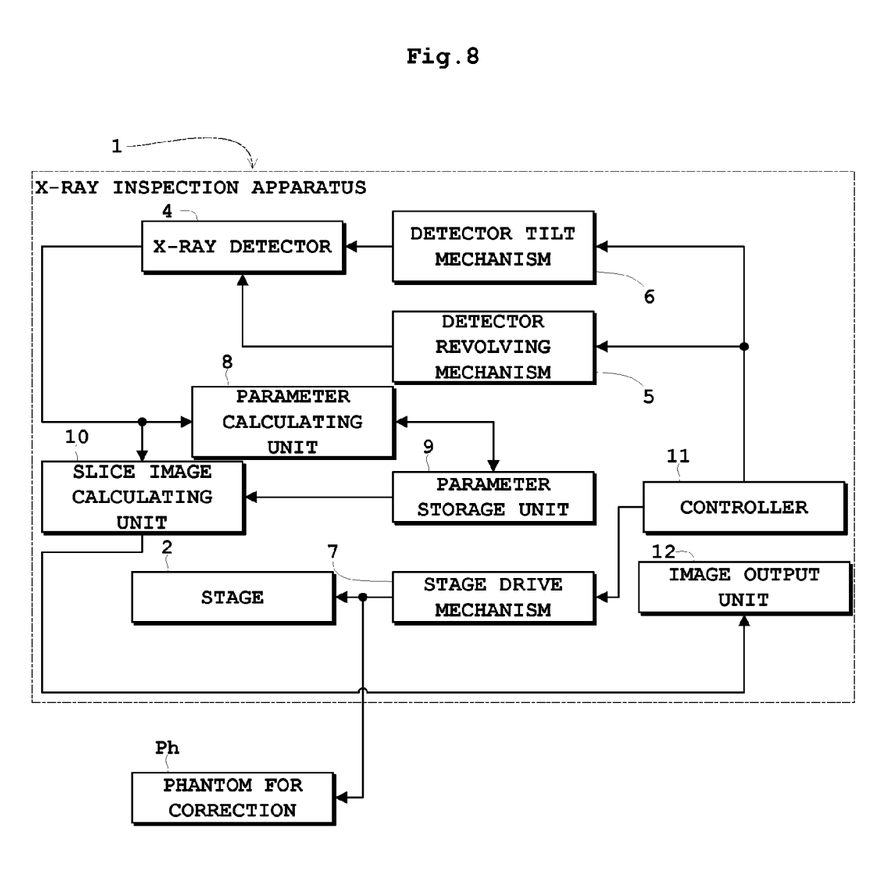
FIG. 8 is a block diagram of the X-ray inspection apparatus according to the embodiment.

FIG. 4 is an outline schematic view of an X-ray inspection apparatus according to the embodiment. FIG. 5 is an outline perspective view of the X-ray inspection apparatus according to the embodiment. FIG. 6 is an outline perspective view of the X-ray inspection apparatus according to the embodiment illustrating a calibration method with a phantom for correction. FIG. 7 is an outline perspective view of the X-ray inspection apparatus according to the embodiment illustrating each coordinate system. FIG. 8 is a block diagram of the X-ray inspection apparatus according to the embodiment. In this embodiment, the X-ray inspection apparatus will be described as an example of radiographic apparatus.

As shown in FIG. 4, the X-ray inspection apparatus 1 includes a stage 2 for holding an object O, and an X-ray tube 3 and an X-ray detector 4 arranged opposite each other across the stage 2. The X-ray detector 4 is not limited to any particular type, but may be an image intensifier (I. I) or a flat panel X-ray detector (FPD). In this embodiment, a flat panel X-ray detector (FPD) will be described as an example of X-ray detector 4. The stage 2 corresponds to the stage in this invention. The X-ray tube 3 corresponds to the radiation emitting device in this invention. The X-ray detector 4 corresponds to the radiation detecting device in this invention.

The FPD has a plurality of detecting elements arranged in a matrix to correspond to pixels, with the detecting elements detecting X-rays and outputting data (charge signals) of the detected X-rays as X-ray detection signals. Thus, the X-ray detector 4 in form of the FPD detects X-rays emitted from the X-ray tube 3 and transmitted through the object O, and outputs the X-ray detection signals. Pixel values based on the X-ray detection signals are arranged as corresponding to the pixels, thereby to acquire a projection image projected to the detecting plane of the X-ray detector 4.

In addition, the X-ray inspection apparatus 1, as shown in FIG. 4, includes a detector revolving mechanism 5 for revolving the X-ray detector 4 about arrow $R_1$, and a detector tilt mechanism 6 for tilting the X-ray detector 4 in the direction of arrow $R_2$. The detector tilt mechanism 6 has an arcuate guide 6a which supports the X-ray detector 4, and a rotary motor (not shown). The rotary motor drives the X-ray detector 4 to tilt in the direction of arrow $R_2$ along the guide 6a.

The detector revolving mechanism 5 is in form of a rotary motor (not shown). The rotary motor rotates the guide 6a of the detector tilt mechanism 6 about arrow $R_1$, thereby to revolve also the X-ray detector 4 supported by the guide 6a about arrow $R_1$. In this embodiment, the detector revolving mechanism 5 revolves the X-ray detector 4 about arrow $R_1$ synchronously with driving of the stage 2. In particular, the detector revolving mechanism 5 revolves the X-ray detector 4 about arrow $R_1$ so that the X-rays emitted from the X-ray tube 3 be transmitted through an attention point on the object O and detected by a central portion of the X-ray detector 4.

In this embodiment, the X-ray tube 3 is fixed to a device casing (not shown), and X-rays broadly emitted from the X-ray tube 3 pass through the attention point on the object O to be detected by the X-ray detector 4.

In addition, the X-ray inspection apparatus 1, as shown in FIG. 8, includes a stage drive mechanism 7 for driving the stage 2 to move straight in the directions of arrows $R_3$, $R_4$ and $R_5$ (see FIGS. 4 and 5), respectively, in world coordinates $X_W$, $Y_W$ and $Z_W$ (see FIGS. 4 and 7) which constitute a rectangular coordinate system, a parameter calculating unit 8 for calculating parameters for correction based on projection images of a phantom Ph for correction (see FIGS. 6, 8, 9A, 9B, 10A and 10B), a parameter storage unit 9 for writing and storing the parameters calculated by the parameter calculating unit 8, a slice image calculating unit 10 for calculating and operating slice images of the object O based on a plurality of projection images and parameters of the object O, a controller 11 for performing overall control of these components, and an image output unit 12 for outputting the slice images obtained by the slice image calculating unit 10 (display output from a monitor or printout from a printer). The stage drive mechanism 7, including the above-mentioned detector revolving mechanism 5 and detector tilt mechanism 6, corresponds to the driving device in this invention. The parameter calculating unit 8 corresponds to the parameter calculating device in this invention. The parameter calculating unit 8 corresponds also to the number of parameters limiting device in this invention. The slice image calculating unit 10 corresponds to the slice image calculating device in this invention.

The stage drive mechanism 7 includes an X-axis linear motor (not shown) which drives the stage 2 to move straight (drives horizontally here) in the direction of arrow $R_3$ (see FIGS. 4 and 5) parallel to $X_W$ (see FIGS. 4 and 7), a Y-axis linear motor (not shown) which drives the stage 2 to move straight (drives horizontally here) in the direction of arrow $R_4$ (see FIG. 5) parallel to $Y_W$ (see FIGS. 4 and 7), and a Z-axis linear motor (not shown) which drives the stage 2 to move straight (drives vertically here) in the direction of arrow $R_5$ (see FIGS. 4 and 5) parallel to $Z_W$ (see FIGS. 4 and 7). In this embodiment, the controller 11 drives the stage 2 to describe a circular path by combination of the paths provided by the X-axis linear motor and Y-axis linear motor, and to synchronize with revolution of the X-ray detector 4 by the detector revolving mechanism 5.

The stage 2 can be fixed to a constant orientation by revolving the X-ray detector 4 while driving the stage 2 on the circular path as noted above. Radiography is conducted in a state as shown in FIG. 6, in which the phantom Ph for correction is placed on the stage 2, and the stage 2 and X-ray detector 4 are driven synchronously as on circular paths about the axis of rotation Ax, shown in a solid line, based on tomographic conditions provided, thereby to acquire a plurality of projection images of the phantom Ph for correction.

Although this embodiment carries out tomography by operation along the circular paths as shown in FIG. 6 (which are the same as the conventional circular paths shown in FIG. 3), the apparatus construction may be the conventional one shown in FIGS. 1-3 as long as it is capable of tomography and it is possible to employ various apparatus constructions for providing paths other than those shown FIGS. 4-7. Since the stage 2, X-ray tube 3 and X-ray detector 4 may operate on the same paths relative to one another, in the case of FIG. 1, for example, the X-ray tube and X-ray detector may be revolved instead of rotating the stage. Not being limited to FIGS. 1-3, there is also no limitation to any particular type of tomography, as exemplified by linear tomography. Thus, as long as it is a mode in which at least one of the radiation emitting device represented by the X-ray tube and the stage is driven, both the radiation emitting device and the stage may be driven, or only the radiation emitting device may be driven, or only the stage may be driven.

As shown in FIG. 7, $W_C$ denotes a world coordinate system, $C_C$ a camera coordinate system, $I_C$ an image plane coordinate system, and $P_C$ a pixel coordinate system. The world coordinate system is a reference coordinate system set arbitrarily, and its origin may be set to the position of object O (see FIGS. 4 and 5) or phantom Ph for correction (see FIGS. 6, 8, 9A, 9B, 10A and 10B). The camera coordinate system is a coordinate system having its origin provided by the X-ray tube 3 (which may be called the light source), $Z_C$-axis extending in the direction of irradiation axis (which may be called the optical axis) from the X-ray tube 3, and $X_C$-axis and $Y_C$-axis corresponding to the horizontal direction and vertical direction on the detecting plane of the X-ray detector 4 (parallel to the x-axis and y-axis of the image plane coordinate system). The image plane coordinate system is a coordinate system having its origin in a position where the optical axis and the detecting plane cross, with the x-axis and y-axis corresponding to the horizontal direction and vertical direction of the detecting plane. The pixel coordinate system is a coordinate system on a pixel-by-pixel basis (pixel unit) with its origin located in an upper left position of each image.

Returning to the description of FIG. 8, the parameter calculating unit 8 calculates parameters for correction based on projection images of the phantom Ph for correction (see FIGS. 6, 9A, 9B, 10A and 10B also), and writes and stores the calculated parameters separately for respective radiographic conditions in the parameter storage unit 9. When correcting slice images of the object O, the parameters are read from the parameter storage unit 9 and the parameters read are used. The parameter storage unit 9 is in form of a storage medium represented by a RAM (Random Access Memory), for example.

Further, initial values of parameters are written and stored in the parameter storage unit 9, and the parameter calculating unit 8 reads the parameters stored in the parameter storage unit 9, updates the parameters, and writes and stores the updated parameters in the parameter storage unit 9. When updating the parameters, only limited parameters are updated. Therefore, the parameter calculating unit 8 has the function of the number of parameters limiting device in this invention. Specific functions of the number of parameters limiting device will be described hereinafter.

The slice image calculating unit 10 calculates slice images of the object O based on a plurality of projection images of the object O and the above-mentioned parameters, and when carrying out this calculation reconstructs the images using parameters suited to radiographic conditions at the time of radiographing the object O. The controller 11 carries out overall control of the respective components of the X-ray inspection apparatus 1, and in particular controls the rotary motor (not shown) of the detector revolving mechanism 5, the rotary motor (not shown) of the detector tilt mechanism 6, and the X-axis, Y-axis and Z-axis linear motors (not shown) of the stage drive mechanism 7, respectively. The above parameter calculating unit 8, slice image calculating unit 10 and controller 11 are provided by a central processing unit (CPU).

By arranging the X-ray tube 3, object O and X-ray detector 4 as shown in FIG. 4, the X-ray tube 3 and X-ray detector 4 can be arranged in an oblique direction inclined by lamino angle as in FIG. 3 to enable radiography (planar CT) from the oblique direction. And the X-ray tube 3 and the stage 2, thus the object O, can be brought close together, thereby to be able to obtain projection images with a high enlargement ratio, without the X-ray tube 3 and object O interfering with each other. Projection images are acquired from a plurality of angles by acquiring a projection image each time the stage 2 is driven, and the slice image calculating unit 10 shown in FIG. 8 calculates and operates slice images based on the plurality of projection images.

Figure 9A:
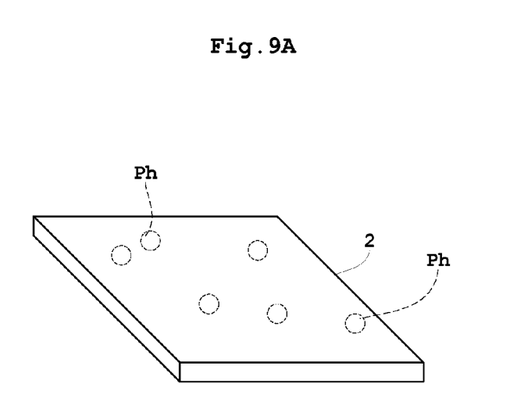
FIG. 9A is a schematic view of an example of stages constructed to carry the phantom for correction at the time of radiography, which is an outline perspective view of the stage with markers embedded therein to act as the phantom for correction.
Figure 9B:
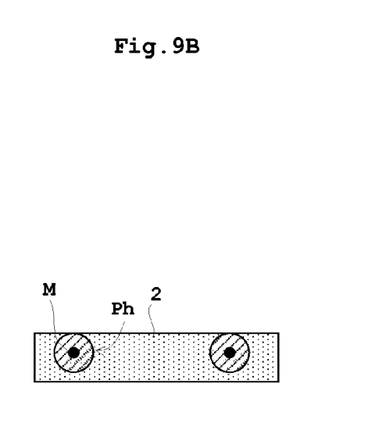
FIG. 9B is a schematic view of the example of stages constructed to carry the phantom for correction at the time of radiography, which is an outline sectional view of FIG. 9A.
Figure 10A:
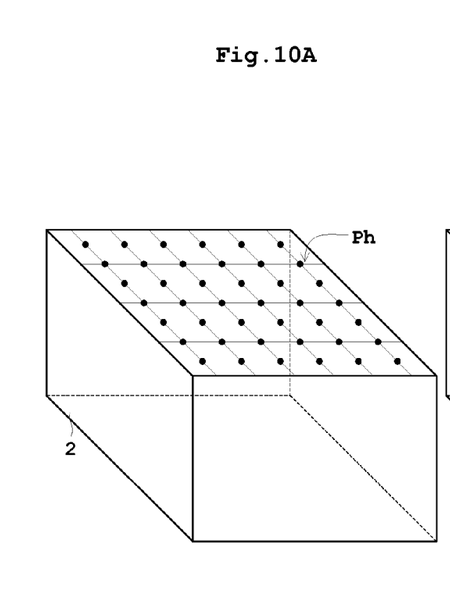
FIG. 10A is a schematic view of another example of stages constructed to carry the phantom for correction at the time of radiography, which is an outline perspective view of the phantom for correction with a pattern installed as markers on a top surface (upper surface) of the stage.
Figure 10B:
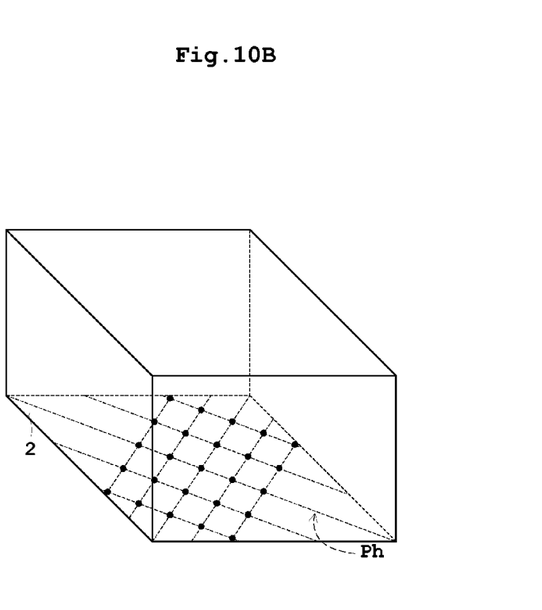
FIG. 10B is a schematic view of another example of stages constructed to carry the phantom for correction at the time of radiography, which is an outline perspective view showing a pattern installed as markers on a reverse surface (lower surface) of the stage.

Next, the phantom Ph for correction will be described with reference to FIGS. 9A, 9B, 10A and 10B. FIGS. 9A and 9B are schematic views of an example of stages constructed to carry the phantom for correction at the time of radiography, in which FIG. 9A is an outline perspective view of the stage with markers embedded therein to act as the phantom for correction, and FIG. 9B is an outline sectional view of FIG. 9A. FIGS. 10A and 10B are schematic views of another example of stages constructed to carry the phantom for correction at the time of radiography, in which FIG. 10A is an outline perspective view of the phantom for correction with a pattern installed as markers on a top surface (upper surface) of the stage, and FIG. 10B is an outline perspective view of the phantom for correction with a pattern installed as markers on a reverse surface (lower surface) of the stage.

As shown in the outline perspective view of FIG. 9A and the outline sectional view of FIG. 9B, the phantom Ph for correction may be embedded in the stage 2. As shown in the outline perspective view of FIG. 10A, the markers in form of a pattern may be installed on the top surface (upper surface) (see FIG. 10A) or the reverse surface (lower surface) (see FIG. 10B) of the stage 2. FIGS. 10A and 10B may be combined to install markers on both the top and reverse surfaces of the stage 2. The markers may be installed on a different surface (side surface, front surface or rear surface).

Generally, since the stage 2 is formed of a material with high radiation transmittance, the markers are formed of a material with low radiation transmittance (eg lead) to distinguish from the stage 2. In the case of FIGS. 9A and 9B, markers M are formed of spherical materials with low radiation transmittance, and the spherical materials are embedded in the stage 2 to act as the phantom Ph for correction.

In the case of FIGS. 10A and 10B, the markers are installed, and the stage 2 is constructed to carry the phantom Ph for correction consisting of the markers. It is to be noted that the markers in FIGS. 10A and 10B can also make intersections of the pattern of the characteristic points, and are therefore included in the concept of markers.

The object O may be used also as the phantom Ph for correction. When the object O is a BGA, for example, markers are installed on certain of the spherical materials (Balls) in the object O. By installing the markers, the object O can serve also as the phantom Ph for correction consisting of the markers, eliminating the necessity to prepare a phantom for correction separately from the object O.

The construction of the stage 2 for carrying the phantoms Ph for correction beforehand as noted above is not limitative. As shown in FIG. 7, the phantom Ph for correction may be placed on the stage 2 only at the time of radiography (when required).

In any case, the phantom Ph for correction enables characteristic points to be extracted from the projection images by image processing, and needs to have a pattern to enable matching of the characteristic points between the projection images. The characteristic points may be spherical central points as shown in FIGS. 9A and 9B, for example, or intersections of a grid as shown in FIGS. 10A and 10B. When parameters are calculated by nonlinear optimization operation (nonlinear optimization method), characteristic points need to be arranged in three dimensions, in the number realizing "number of characteristic points×2×number of frames>number of characteristic points×3+number of parameters×number of frames".

Figure 11:
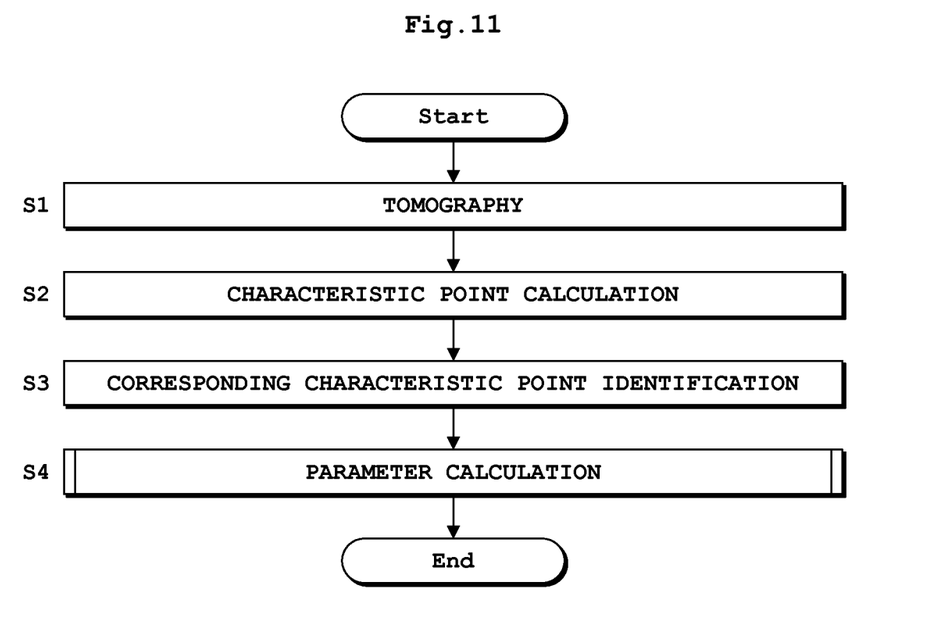
FIG. 11 is a flow chart showing a series of processes up to calculation of parameters from projection images of the phantom for correction.
Figure 12:
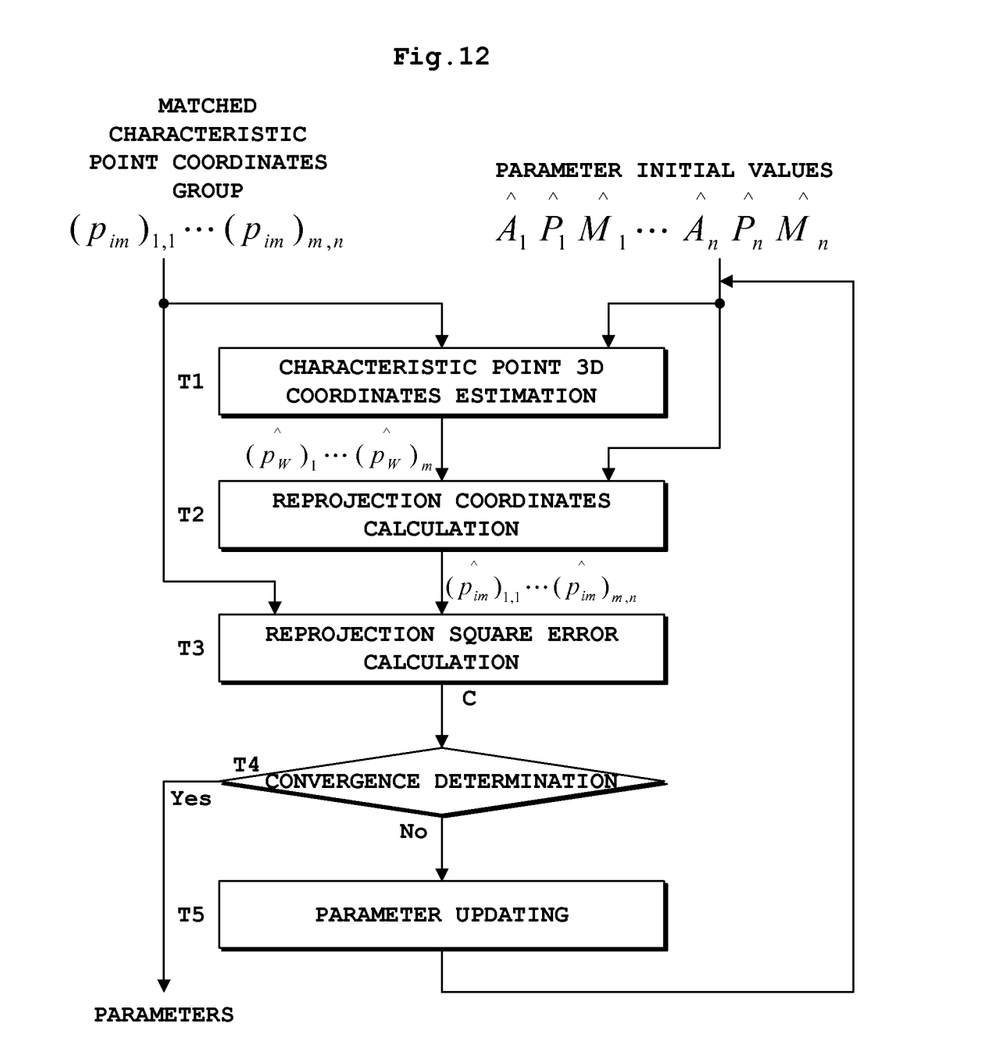
FIG. 12 is a specific flow chart of the parameter calculation in FIG. 11.

Next, calibration (correction) with a phantom for correction will be described with reference to FIGS. 11 and 12. FIG. 11 is a flow chart showing a series of processes up to calculation of parameters from projection images of the phantom for correction. FIG. 12 is a specific flow chart of the parameter calculation in FIG. 11.

(Step S1) Tomography

As shown in FIG. 6, the phantom Ph for correction is placed on the stage 2, and radiography is performed to acquire a plurality of slice images of the phantom Ph for correction. Regarding the scanning track at this time, driving may be made on the same scanning track as at the time of carrying out tomography of the object O (see FIGS. 4 and 5). Regarding the number of radiographic frames, it is preferable to acquire at least the same number of frames as when carrying out tomography of the object O.

(Step S2) Characteristic Point Calculation

Characteristic points are extracted from the projection images of the phantom Ph for correction acquired in step S1, and characteristic point coordinates are calculated. There are various methods of characteristic point extraction, and the invention is not limited to a particular one. When radiographing the phantom Ph for correction which has spherical markers as shown in FIGS. 9A and 9B, for example, it is conceivable to extract the centers of the balls as characteristic points. As the centers of the balls at this time, center positions of the balls may be calculated using a morphology operation represented by opening process or erosion process, or local maximum coordinates of range images may be calculated as center positions by distance transform, for example, using information on pixel values (luminance values).

(Step S3) Corresponding Characteristic Point Identification

The characteristic points calculated in step S2 are matched between the frames. As a matching method, it is conceivable to use the characteristic that, with frames continual in time, corresponding characteristic points exist close to one another on the images, and to regard the points having characteristic point coordinates close to one another as corresponding characteristic points.

(Step S4) Parameter Calculation

Parameters are calculated from the characteristic point coordinates matched in step S3. The parameter calculation at this time has the same problem setting as camera calibration known in the field of computer vision, as noted hereinbefore, and a method such as Bundle Adjustment is known as calculation algorithm. The Bundle Adjustment method is a technique for calculating three-dimensional coordinates of characteristic points and parameters of a geometric model at the time of radiography by nonlinear optimization operation, as noted hereinbefore.

Specifically, when a perspective projection model is considered, to define each coordinate system shown in FIG. 7, the transform from the world coordinate system to the pixel coordinate system regarding the characteristic points is expressed by homogeneous coordinates as in the following equation (1):

[Math 1]

$$(p_{im})_{i,j} = A_j P_j M_j (p_W)_i$$

$$p_W = [X_W Y_W Z_W 1]^T : \quad (1)$$

three-dimensional homogeneous coordinates of the characteristic points in the world coordinate system $$p_{im} = [x_{im} y_{im} 1]^T :$$

two-dimensional homogeneous coordinates of the characteristic points in the pixel coordinate system $$M = \begin{bmatrix} R & t \\ 0 & 1 \end{bmatrix}$$

transform matrix M (transform matrix from the world coordinate system to the camera coordinate system)

$$P = \begin{bmatrix} f & 0 & 0 & 0 \\ 0 & f & 0 & 0 \\ 0 & 0 & 1 & 0 \end{bmatrix}$$

transform matrix P (transform matrix from the camera coordinate system to the image plane coordinate system)

$$A = \begin{bmatrix} k_x & skew & \sigma_x \\ 0 & k_y & \sigma_y \\ 0 & 0 & 1 \end{bmatrix}$$

transform matrix A (transform matrix from the image plane coordinate system to the pixel coordinate system)
i: coordinates of the characteristic points, and j: frame number Matrix R in matrix M is a rotation matrix of three rows and three columns, and has three degrees of freedom of rotation ($\theta_x$, $\theta_y$, $\theta_z$). Vector t is a translation vector of three rows and one column, and has three degrees of freedom of translation ($t_x$, $t_y$, $t_z$). That is, matrix M consists of six parameters.

Matrix P has parameter f indicating a distance (that is, SID) a perpendicular is drawn from the X-ray tube 3 (see FIG. 4), i.e. the light source, to the X-ray detector 4 (see FIGS. 4 and 5).

Matrix A consists of a total of five parameters, which are scale variables $k_x$ and $k_y$ for transformation to pixel units, $\sigma_x$ and $\sigma_y$ indicating an origin position relationship between the image plane coordinate system and the pixel coordinate system, and skew indicating an angle between x-axis and y-axis of the pixel coordinate system.

That is, with the perspective projection model, the transformation from the world coordinate system to the pixel coordinate system is expressed by parameters (degrees of freedom being 11) representing 12 geometric relationships. The Bundle Adjustment method calculates these parameters.

FIG. 12 is a specific flow chart of the parameter calculation of FIG. 11, which shows a parameter calculation processing flow by the Bundle Adjustment method. Steps T1-T5 in FIG. 12 correspond to the parameter calculating step in this invention. Initial values of the parameters may be set based on tomographic conditions, or certain appropriate parameters calculated in a previous calibration may be set as initial values of the parameters.

(Step T1) Characteristic Point Three-Dimensional Coordinates Estimation

Estimation is made of three-dimensional coordinates of the characteristic points from the matched characteristic points (indicated "matched characteristic point coordinates group" in FIG. 12) $(p_{im})_{1,1} \ldots (p_{im})_{m,n}$ and parameter initial values $\hat{A}_1 \hat{P}_1 \hat{M}_1 \ldots \hat{A}_n \hat{P}_n \hat{M}_n$. In this step T1, initial values $\hat{A}_1 \hat{P}_1 \hat{M}_1 \ldots \hat{A}_n \hat{P}_n \hat{M}_n$ of all the parameters are inputted. This step T1 corresponds to the characteristic point three-dimensional coordinates estimating step. The transform matrices in equation (1) above may be rewritten with $\hat{z}_j = \hat{A}_j \hat{P}_j \hat{M}_j$ for extension to the case of n frames, as in the following equation (2):

[Math 2]

$$(P_{im})_i = \hat{Z}(p_W)_i \quad (2)$$

where $$(P_{im})_i = \begin{bmatrix} (p_{im})_{i,1} \\ \vdots \\ (p_{im})_{i,n} \end{bmatrix}, \hat{Z} = \begin{bmatrix} \hat{z}_1 \\ \vdots \\ \hat{z}_n \end{bmatrix}$$

$\hat{A}_j$: indicated $\hat{A}_j$ in the specification
$\hat{P}_j$: indicated $\hat{P}_j$ in the specification
$\hat{M}_j$: indicated $\hat{M}_j$ in the specification
$\hat{Z}_j$: indicated $\hat{z}_j$ in the specification By calculating pseudo inverse matrices from equation (2) above, least squares solution $(\hat{p}_W)_i$ of the characteristic point three-dimensional coordinates can be obtained from the following equation (3):

[Math 3]

$$(\hat{p}_W)_i = (\hat{Z}^T \hat{Z})^{-1} \hat{Z}^T (P_{im})_i \quad (3)$$

$(\hat{P}_W)_i$: indicated $(\hat{p}_W)_i$ in the specification (Step T2) Reprojection Coordinates Calculation By substituting the characteristic point three-dimensional coordinates $\hat{p}_W$ estimated in step T1 into equation (2) above, reprojection coordinates $(\hat{p}_{im})_{1,1} \ldots (\hat{p}_{im})_{m,n}$ can be obtained. This step T2 corresponds to the reprojection coordinates calculating step.

(Step T3) Reprojection Square Error Calculation

Reprojection square errors C are calculated by the following equation (4) from the reprojection coordinates $(\hat{p}_{im})_{1,1} \ldots (\hat{p}_{im})_{m,n}$ calculated in step T2, and the matched characteristic points $(p_{im})_{1,1} \ldots (p_{im})_{m,n}$. This step T3 corresponds to the reprojection square error calculating step.

[Math 4]

$$C = \sum_{i=1}^{m} \sum_{j=1}^{n} \left( (p_{im})_{i,j} - (\hat{p}_{im})_{i,j} \right)^2 \quad (4)$$

$(\hat{P}_{im})_{i,j}$: indicated $(\hat{p}_{im})_{i,j}$ in the specification (Step T4) Convergence Determination A determination is made whether the values of reprojection square errors C calculated in step T3 have converged or not. This step T4 corresponds to the convergence determining step. When the values of reprojection square errors C have sufficiently converged, the parameters at this time are regarded as parameters finally limited in number, and the series of flows is ended.

(Step T5) Parameter Updating

When the values of reprojection square errors C have not sufficiently converged, the parameters are updated to lessen the values of C. This step T5 corresponds to the parameter updating step. The parameter updating method is a matter generally handled in the field of nonlinear optimization, and includes various methods such as Levenberg-Marquardt Method.

When all the parameters are considered unknown, the number of variables estimated by Bundle Adjustment method is (number of characteristic points×3+number of parameters×number of frames) as noted hereinbefore. As noted hereinbefore in the section "Technical Problem", the nonlinear optimization operation has a problem that the larger number of variables results in the longer computation time. So, by using information on tomography (radiographic conditions), computation is speeded up by reducing and limiting the number of variables to be estimated, while securing convergence accuracy. Therefore, when updating the parameters in step T5, only the parameters limited beforehand based on radiographic conditions are updated, resulting in a reduced number of parameters to be updated.

When initial values are set from tomographic conditions in the nonlinear optimization operation, an error between initial value and true value can be said a combination of an assembly error between the design drawing of an apparatus and an actual apparatus, and a drive error of the drive line. Regarding a parameter with which an error occurs due to an assembly error, a single calibration will enable its use also when tomographic conditions have been changed. Therefore, when all the parameters are estimated just once by nonlinear optimization operation, and calibration is carried out again after tomographic conditions are changed, the number of variables can be reduced, while securing convergence accuracy, by performing a nonlinear optimization operation limited to the parameters with which errors occur due to an assembly error.

When a drive error has occurred in each drive line, it is seen from equation (4) above that the influence of these drive errors on the projection images influences convergence. Since radiography is fluoroscopy, enlarged images are projected to the X-ray detector 4. Therefore, the influence of a drive error of the stage 2 appears on the X-ray detector 4 in an enlargement corresponding to an enlargement ratio. Since, on the other hand, the influence of a drive error of the X-ray detector 4 is not enlarged, the driving accuracy of the stage 2 is more important for improvement in convergence performance. So, for example, by limiting the parameters to be estimated to parameters $\theta_x$, $\theta_y$, $\theta_z$, $t_x$, $t_y$ and $t_z$ relating to the drive accuracy of the stage 2, worsening of convergence accuracy can be inhibited and the number of variables can be reduced.

When the stage 2 is constructed of linear drive elements (straight drive elements), it is thought that the coordinate system is little likely to incline only if a drive shaft is firmly fixed to the apparatus. So, by limiting the parameters to be estimated to the three translation parameters $t_x$, $t_y$ and $t_z$, worsening of convergence accuracy can be inhibited and the number of variables can be reduced.

As noted above, the drive accuracy of the stage 2 is the more important, with the higher enlargement ratio radiography conducted. When tomography is carried out by PCT with a high enlargement ratio, the importance of the drive accuracy of the stage 2 will increase relative to the drive accuracy of the X-ray detector 4. That is, since there is a less difference in convergence performance between the case of limiting the parameters to the above translation parameters $t_x$, $t_y$ and $t_z$ and the case of not limiting so, worsening of the convergence accuracy can be inhibited and the number of variables can be reduced with increased effect.

Steps S2-S4 in FIG. 11 are executed by the parameter calculating unit 8 (see FIG. 8). The parameter calculating unit 8 executes also steps T1-T5 in FIG. 12. When the parameter calculating unit 8 updates the parameters, only limited parameters are updated. The process of reducing and limiting the number of parameters corresponds to the number of parameters limiting step in this invention.

The slice image calculating unit 10 (see FIG. 8) calculates slice images by carrying out back projection of the projection images of the object O. A slice image calculation algorithm includes known methods, and the FBP method (Filtered Back Projection method), for example, is known.

According to the X-ray inspection apparatus in this embodiment having the above construction and the image processing method therefor, the parameter calculating unit 8, based on a plurality of projection images of a phantom Ph for correction, calculates parameters representing a geometric relationship between the radiation emitting device (X-ray tube 3 in this embodiment), the stage 2 and the radiation detecting device (X-ray detector 4 in this embodiment) by nonlinear optimization operation. Based on a plurality of projection images of an object O and the above parameters (correction parameters), the slice image calculating unit 10 calculates slice images of the object O, and when carrying out this calculation, reconstructs the images using parameters suited to radiographic conditions at the time of radiographing the object O. At the time of this parameter calculation, based on the radiographic conditions when the phantom Ph for correction is radiographed, the number of parameters limiting device (parameter calculating unit 8 in this embodiment) reduces and limits the number of parameters to be calculated by nonlinear optimization operation. Thus, based on the known radiographic conditions, initial values of the parameters representing the geometric relationship between the radiation emitting device (X-ray tube 3), stage 2 and radiation detecting device (X-ray detector 4) are estimated, and the nonlinear optimization operation is carried out on only the parameters considered, in view of mechanisms and drive characteristics of the apparatus, to have large errors between the initial values of the parameters and the parameters at the time when radiography is actually carried out. As a result, the calculation can be speeded up, while securing the convergence accuracy of the nonlinear optimization operation, by using the radiographic conditions, i.e. information on tomography.

Preferably, in this embodiment, when the radiographic conditions have been changed, the number of parameters limiting device (parameter calculating unit 8) described above reduces and limits the number of parameters calculated by nonlinear optimization operation, based on the changed radiographic conditions. For example, a nonlinear optimization operation is carried out just once after shipment or after installation of the apparatus, and the number of parameters is reduced and limited based on the changed radiographic conditions when the radiographic conditions have been changed. Not only drive errors of the drive line, but there exist installation errors occurring at the time of shipment and installation of each constituent element of the radiographic apparatus (X-ray inspection apparatus 1 in this embodiment), which become errors in the initial values of the parameters. So, parameters including the installation errors are calculated by carrying out a nonlinear optimization operation just once after shipment or after installation of the apparatus, and estimation is made of only the parameters of portions relevant to the drive errors of the drive line when the radiographic conditions have been changed.

As noted hereinbefore in the section "Solution to Problem", the timing of reducing and limiting the number of parameters is not limited only to the time when the radiographic conditions are actually changed. Since, for example, it is possible that drive errors of the drive line occur at the time the apparatus is powered on, the number of parameters may be reduced and limited based on the radiographic conditions at the power-on time after each operation to switch on the apparatus. A setting for reducing and limiting the number of parameters may be carried out automatically by the central processing unit (CPU) (controller 11 in this embodiment) or the like which determines that the radiographic conditions have been changed, or manually by the operator, or by combination of the automatic and manual operations.

Preferably, in this embodiment, the number of parameters limiting device (parameter calculating unit 8) described above limits the parameters calculated by nonlinear optimization operation to three parameters (translation parameters $t_x$, $t_y$ and $t_z$ in this embodiment) representing a coordinates positional relationship between the radiation emitting device (X-ray tube 3) and stage 2. In a triaxial drive (with the X-ray tube 3 fixed, and the stage 2 driven only horizontally and vertically in this embodiment), for example, it is possible to set a limitation to the three parameters (translation parameters $t_x$, $t_y$ and $t_z$) when an enlargement ratio is changed, and when changing the distance (SID: Source Image Distance) a perpendicular is drawn from the radiation emitting device (X-ray tube 3) to the radiation detecting device (X-ray detector 4). Since radiography is fluoroscopy, enlarged images are necessarily projected to the radiation detecting device (X-ray detector 4). Therefore, the influence of drive errors of the radiation emitting device (X-ray tube 3) and the stage 2 on the projection images is greater than the influence of drive errors of the radiation detecting device (X-ray detector 4) on the projection images. So, while securing the convergence accuracy of nonlinear optimization operation, the operation can be speeded up, by performing calculations limited to the three parameters (translation parameters $t_x$, $t_y$ and $t_z$) representing the coordinates positional relationship between the radiation emitting device (X-ray tube 3) and the stage 2, which have a great influence.

In particular, that the driving device (stage drive mechanism 7 in this embodiment) rotates the stage 2, with an axis perpendicular to the surface of stage 2 set as the axis of rotation Ax as in this embodiment can be applied to the case of planar CT (PCT: Planar Computed Tomography) which emits radiation (X-rays in this embodiment) from the radiation emitting device (X-ray detector 4) in an oblique direction inclined by lamino angle from the axis of rotation Ax. In planar CT (PCT), radiography can be performed with a higher enlargement ratio than in ordinary CT. With the higher enlargement ratio, the greater influence is exerted on projection images by drive errors of the radiation emitting device (X-ray detector 4) or the stage 2. This reduces an adverse influence on the convergence accuracy of evaluation functions due to the limitation to the three parameters (translation parameters $t_x$, $t_y$ and $t_x$).

The specifics of the image processing method according to this embodiment are as follows. Specifically, a parameter calculating step (steps T1-T5 in FIG. 12) is provided for calculating the above-mentioned parameters by nonlinear optimization operation. The parameter calculating step (steps T1-T5) includes a characteristic point three-dimensional coordinates estimating step (step T1), a reprojection coordinates calculating step (step T2), a reprojection square error calculating step (step T3), a convergence determining step (step T4) and a parameter updating step (step T5). In the parameter updating step (step T5), only limited parameters are updated. In the characteristic point three-dimensional coordinates estimating step (step T1), based on characteristic points extracted from projection images of the phantom for correction and initial values of the parameters, three-dimensional coordinates of the characteristic points are estimated. In the reprojection coordinates calculating step (step T2), reprojection coordinates are calculated based on the characteristic point three-dimensional coordinates estimated in the characteristic point three-dimensional coordinates estimating step (step T1). In the reprojection square error calculating step (step T3), reprojection square errors are calculated based on the reprojection coordinates calculated in the reprojection coordinates calculating step (step T2) and the above characteristic points. In the convergence determining step (step T4), convergence determination is made of the reprojection square errors calculated in the reprojection square error calculating step (step T3). And in the parameter updating step (step T5), when values of the reprojection square errors have not converged, the parameters are updated to reduce the values of the reprojection square errors, and at the time of this updating, only limited parameters are updated. Thus, at the time of parameter updating, the number of parameters to be calculated is limited beforehand based on radiographic conditions. This can reduce the number of parameters to be updated in the parameter updating step (step T5), and calculation can be speeded up while securing the convergence accuracy of the nonlinear optimization operation.

This invention is not limited to the foregoing embodiment, but may be modified as follows:

(1) In the foregoing embodiment, an X-ray inspection apparatus has been described as an example of radiographic apparatus. However, the radiation is not limited to X-rays as long as the apparatus performs radiography based on projection images obtained by detecting, with a radiation detecting device, radiation emitted from a radiation emitting device and transmitted through an object. Radiation other than X-rays may be used (such as α-rays, β-rays, γ-rays or the like).

(2) In the foregoing embodiment, radiography may be performed on any objects exemplified by a mounted substrate, a through hole/pattern/solder joint of a multilayer substrate, an electronic component before mounting such as an integrated circuit (IC) arranged on a palette, a casting such as of metal, or a molded article such as a videocassette recorder, as noted hereinbefore.

REFERENCE SIGNS LIST

2 . . . stage
3 . . . X-ray tube
4 . . . X-ray detector
7 . . . stage drive mechanism
8 . . . parameter calculating unit
10 . . . slice image calculating unit
$t_x$, $t_y$ and $t_z$ . . . translation parameters
O . . . object

The invention claimed is:

1. A radiographic apparatus for performing radiography, comprising:
a stage for holding an object; and
an x-ray radiation emitting device and an x-ray radiation detecting device arranged opposite each other across the stage;
the radiography being performed based on projection images obtained by detecting, with the x-ray radiation detecting device, x-ray radiation emitted from the x-ray radiation emitting device and transmitted through the object;
the apparatus further comprising:
a driving device for driving at least one of the x-ray radiation emitting device and the stage in a state where the object or a phantom for correction is placed on the stage;
a parameter calculating device for calculating parameters representing a geometric relationship among the x-ray radiation emitting device, the stage and the x-ray radiation detecting device by nonlinear optimization operation based on a plurality of projection images of the phantom for correction;
a slice image calculating device for calculating slice images of the object based on a plurality of projection images of the object and the parameters, and when carrying out the calculation, reconstructing the images using those of the parameters suited to radiographic conditions at a time of radiographing the object; and
a number of parameters limiting device for reducing and limiting, when calculating the parameters, the number of parameters calculated by nonlinear optimization operation, based on radiographic conditions at a time of radiographing the phantom for correction, wherein
only the parameters limited are updated when the parameters are updated.

2. The radiographic apparatus according to claim 1 wherein, when radiographic conditions have been changed, the number of parameters limiting device reduces and limits the number of parameters calculated by nonlinear optimization operation, based on the changed radiographic conditions.

3. The radiographic apparatus according to claim 1 wherein the number of parameters limiting device limits the parameters calculated by nonlinear optimization operation to three parameters representing a coordinates positional relationship between the x-ray radiation emitting device and the stage.

4. The radiographic apparatus according to claim 3 wherein:
the driving device rotates the stage with an axis perpendicular to a surface of the stage set as an axis of rotation; and
planar CT is performed to emit the x-ray radiation from the x-ray radiation emitting device in an oblique direction inclined by lamino angle from the axis of rotation.

5. An image processing method for a radiographic apparatus for performing radiography, the apparatus comprising:
a stage for holding an object; and
an x-ray radiation emitting device and an x-ray radiation detecting device arranged opposite each other across the stage;
the radiography being performed based on projection images obtained by detecting, with the x-ray radiation detecting device, x-ray radiation emitted from the x-ray radiation emitting device and transmitted through the object;
the method comprising:
a number of parameters limiting step executed when calculating parameters representing a geometric relationship among the x-ray radiation emitting device, the stage and the x-ray radiation detecting device by nonlinear optimization operation based on a plurality of projection images of a phantom, for reducing and limiting the number of parameters calculated by the nonlinear optimization operation, based on radiographic conditions at a time of radiographing the phantom for correction, wherein
only the parameters limited are updated when the parameters are updated.

6. The image processing method for the radiographic apparatus according to claim 5 comprising:
a parameter calculating step for calculating the parameters by nonlinear optimization operation;
the parameter calculating step including:
a characteristic point three-dimensional coordinates estimating step for estimating, based on characteristic points extracted from projection images of the phantom for correction and initial values of the parameters, three-dimensional coordinates of the characteristic points;
a reprojection coordinates calculating step for calculating reprojection coordinates based on the characteristic point three-dimensional coordinates estimated in the characteristic point three-dimensional coordinates estimating step;
a reprojection square error calculating step for calculating reprojection square errors based on the reprojection coordinates calculated in the reprojection coordinates calculating step and the characteristic points;
a convergence determining step for making convergence determination of the reprojection square errors calculated in the reprojection square error calculating step; and
a parameter updating step, when values of the reprojection square errors have not converged, for updating the parameters to reduce the values of the reprojection square errors;
wherein the parameter updating step is executed to update only the parameters limited in the number of parameters limiting step.

* * * * *